(12) United States Patent
Jeong et al.

(10) Patent No.: US 10,109,044 B2
(45) Date of Patent: Oct. 23, 2018

(54) APPARATUS FOR MEASURING MICRO-CRACKS IN A MEMBRANE ELECTRODE ASSEMBLY AND METHOD FOR PREDICTING GENERATION OF MICRO-CRACKS IN THE SAME

(71) Applicants: Hyundai Motor Company, Seoul (KR); Korea Advanced Institute of Science and Technology, Daejeon (KR)

(72) Inventors: Byeong-Heon Jeong, Gyeonggi-do (KR); Bo Ki Hong, Seoul (KR); Jong Kil Oh, Gyeonggi-do (KR); Taek-Soo Kim, Daejeon (KR); Sanwi Kim, Gyeonggi-do (KP); Kyung-Rim Jang, Gyeonggi-do (KR)

(73) Assignees: Hyundai Motor Company, Seoul (KR); Korea Advanced Institute of Science and Technology, Daejeon (KR)

( * ) Notice: Subject to any disclaimer, the term of this patent is extended or adjusted under 35 U.S.C. 154(b) by 275 days.

(21) Appl. No.: 14/942,390

(22) Filed: Nov. 16, 2015

(65) Prior Publication Data

US 2017/0003239 A1 Jan. 5, 2017

(30) Foreign Application Priority Data

Jul. 1, 2015 (KR) .................. 10-2015-0094079

(51) Int. Cl.
*G06T 7/00* (2017.01)
*G01N 21/95* (2006.01)
(Continued)

(52) U.S. Cl.
CPC ............. *G06T 7/0004* (2013.01); *G01N 3/08* (2013.01); *G01N 21/8422* (2013.01);
(Continued)

(58) Field of Classification Search
CPC ...... G01N 27/041; G01N 27/06; G01N 27/20; G01N 27/02; G01N 27/04
(Continued)

(56) References Cited

U.S. PATENT DOCUMENTS 2,921,257 A * 1/1960 Boicey .................... C03C 17/25
324/693
8,358,137 B2 * 1/2013 Uchiyama ......... H01M 8/04197
324/459
(Continued)

FOREIGN PATENT DOCUMENTS

JP 2005-091167 A 4/2005
JP 2010108815 A * 5/2010
(Continued)

OTHER PUBLICATIONS

De Moor, G., et al. "Understanding membrane failure in PEMFC: comparison of diagnostic tools at different observation scales." Fuel Cells 12.3 (2012): 356-364.*

(Continued)

*Primary Examiner* — Christopher McAndrew
(74) *Attorney, Agent, or Firm* — Mintz Levin Cohn Ferris Glovsky and Popeo, P.C.; Peter F. Corless

(57) ABSTRACT

An apparatus for measuring micro-cracks in a membrane electrode assembly includes a resistance measurement unit to measure variation in electrical resistance of the membrane electrode assembly while tensioning the membrane electrode assembly in a state in which power is applied to an upper catalyst layer while a lower catalyst layer is insulated, an image capture unit to capture an image of micro-cracks in the upper catalyst layer while the membrane electrode assembly is being tensioned, and a controller to detect, in real time, variation in electrical resistance measured by the resistance measurement unit, corresponding to the image of micro-cracks captured by the image capture unit, and to (Continued)

interpret the size of the micro-cracks generated in the membrane electrode assembly based on the detected variation in electrical resistance.

7 Claims, 4 Drawing Sheets

(51) Int. Cl.
  G01N 3/08 (2006.01)
  H01M 8/00 (2016.01)
  G01N 21/84 (2006.01)
  G01N 27/20 (2006.01)
(52) U.S. Cl.
  CPC ........... *G01N 21/95* (2013.01); *G01N 27/205* (2013.01); *H01M 8/00* (2013.01); *G01N 2203/0066* (2013.01); *G06T 2207/10056* (2013.01); *G06T 2207/30108* (2013.01)
(58) Field of Classification Search
  USPC ........................................................ 324/693
  See application file for complete search history.

(56) References Cited

U.S. PATENT DOCUMENTS

| | | | | |
|---|---|---|---|---|
| 8,500,985 | B2* | 8/2013 | Mayer | C25F 5/00 205/112 |
| 2004/0241522 | A1* | 12/2004 | Ono | C08G 77/04 429/494 |
| 2007/0212587 | A1* | 9/2007 | Fragiadakis | F16J 15/14 429/483 |
| 2009/0071838 | A1* | 3/2009 | Murphy | A61L 2/183 205/337 |
| 2009/0214930 | A1* | 8/2009 | Charlat | H01M 8/0273 429/450 |
| 2009/0280243 | A1* | 11/2009 | Mayer | C25F 5/00 427/154 |
| 2011/0060536 | A1* | 3/2011 | Feng | G01N 27/041 702/35 |
| 2011/0281198 | A1* | 11/2011 | Iwamura | H01M 8/0276 429/482 |
| 2014/0134518 | A1* | 5/2014 | Smith | B01D 67/0009 429/483 |
| 2014/0361797 | A1* | 12/2014 | Chuang | B01D 61/427 324/693 |

FOREIGN PATENT DOCUMENTS

| | | |
|---|---|---|
| JP | 2010108815 A1 * | 5/2010 |
| JP | 2011-022140 A | 2/2011 |
| KR | 10-2004-0095537 A | 11/2004 |
| KR | 2009-0049847 A | 5/2009 |
| KR | 10-2012-0027752 A | 3/2012 |
| KR | 10-2014-0108968 A | 9/2014 |
| KR | 10-1531177 B1 | 6/2015 |

OTHER PUBLICATIONS

Translation of JP2010108815.*
Yousfi-Steiner, N., et al. "A review on polymer electrolyte membrane fuel cell catalyst degradation and starvation issues: Causes, consequences and diagnostic for mitigation." Journal of Power Sources 194.1 (2009): 130-145.*

* cited by examiner

US 10,109,044 B2

APPARATUS FOR MEASURING MICRO-CRACKS IN A MEMBRANE ELECTRODE ASSEMBLY AND METHOD FOR PREDICTING GENERATION OF MICRO-CRACKS IN THE SAME

CROSS-REFERENCE TO RELATED APPLICATION

This application claims under 35 U.S.C. § 119(a) the benefit of Korean Patent Application No. 10-2015-0094079, filed on Jul. 1, 2015, in the Korean Intellectual Property Office, the entire contents of which are incorporated by reference herein.

BACKGROUND

1. Field of the Invention

The present invention relates to an apparatus for measuring micro-cracks in a membrane electrode assembly and a method for predicting the generation of micro-cracks in the membrane electrode assembly and, more particularly, to an apparatus for measuring micro-cracks in the membrane electrode assembly for a fuel cell, which is formed on an upper surface and a lower surface thereof, and includes an upper conductive catalytic layer and a lower conductive catalytic layer, respectively, and a method for predicting the generation of micro-cracks in the membrane electrode assembly.

2. Description of the Related Art

A stack for a fuel cell is generally comprised of hundreds of unit cells. Each unit cell includes, for example, a Membrane Electrode Assembly (MEA), a Gas Diffusion Layer (GDL), and a separator, and plays an important role in the generation of electricity. Among the constituent components of the unit cell, electrodes of the membrane electrode assembly are formed on respective surfaces of the membrane electrode assembly, i.e. the upper surface and the lower surface thereof. These electrodes are present in a Pt/C form, in which the surfaces of carbon particles are covered with a catalyst such as, for example, platinum. Substantially, a chemical reaction occurs when supplied reaction gas, i.e. hydrogen, oxygen, or air including the same meets the catalyst layer, thus generating water and electricity, which are the outputs of the reaction.

FIG. 1 (RELATED ART) is a view illustrating the basic configuration of a membrane electrode assembly for a fuel cell, and FIG. 2 (RELATED ART) is an SEM analytic image illustrating the configuration of the membrane electrode assembly for the fuel cell.

The membrane electrode assembly, as exemplarily illustrated in FIG. 1, includes a polymer electrolyte membrane, which transfers protons, and catalyst layers which are present in the form of coatings on both surfaces of the polymer electrolyte membrane. Each of the catalyst layers consists of an electrically conductive carbon support and a platinum catalyst.

The catalyst layers exhibit structural vulnerability, particularly, under severe fuel cell operating conditions, and are susceptible to the generation of micro-cracks as the operating time increases. Once the micro-cracks have been generated, the micro-cracks become large cracks as time passes.

For example, when the stack of the fuel cell repeatedly experiences a cyclic dry/wet or freezing/thawing environment, micro-cracks are first generated in the catalyst layers. Then, the cracks grow as the operating time increases, thereby consequently having a very negative effect on the durability of the stack.

That is, although the generation of micro-cracks in the catalyst layers has been recognized as an important factor that may determine the lifespan of a fuel cell vehicle, technical developments to quantitatively and accurately evaluate the generation and growth of micro-cracks have not been implemented according to the related art.

Meanwhile, various methods for measuring micro-cracks have been proposed and used in the related art. For example, micro-cracks have been measured via various nondestructive inspection methods such as, for example, ultrasonic inspection, radiographic inspection, liquid permeation inspection, and thermal inspection methods.

However, these nondestructive inspection methods merely verify the presence of cracks, but cannot measure the generation and growth of micro-cracks, and thus are difficult to apply to composite materials, such as the membrane electrode assembly for the fuel cell.

SUMMARY

Therefore, the present invention provides an apparatus for measuring micro-cracks in a membrane electrode assembly for a fuel cell, which is capable of checking whether micro-cracks are generated in catalyst layers of the membrane electrode assembly and measuring the size of micro-cracks in real time, and a method for predicting the generation of micro-cracks in a membrane electrode assembly which is capable of measuring the extent of growth of micro-cracks generated in catalyst layers of the membrane electrode assembly using data that is measured and captured by the apparatus.

In accordance with one aspect of the present invention, the above and other objects can be accomplished by the provision of an apparatus for measuring micro-cracks in a membrane electrode assembly for a fuel cell, the membrane electrode assembly being formed with an upper catalytic layer and a lower catalytic layer on an upper surface and a lower surface of a polymer electrolyte membrane, respectively, including a resistance measurement unit configured to clamp the upper catalyst layer and the lower catalyst layer of the membrane electrode assembly, the resistance measurement unit serving to measure variation in electrical resistance of the membrane electrode assembly while tensioning both sides of the membrane electrode assembly in a state in which power is applied to only the upper catalyst layer of the membrane electrode assembly while the lower catalyst layer of the membrane electrode assembly is insulated, an image capture unit disposed directly above the membrane electrode assembly and serving to capture an image of micro-cracks generated in the upper catalyst layer of the membrane electrode assembly while the membrane electrode assembly is being tensioned by the resistance measurement unit, and a controller configured to detect, in real time, the variation in electrical resistance, measured by the resistance measurement unit, corresponding to the image of micro-cracks captured by the image capture unit, and to interpret the size of the micro-cracks generated in the membrane electrode assembly based on the detected variation in electrical resistance.

The resistance measurement unit may include a pair of clampers configured to clamp both sides of the membrane electrode assembly in the state in which power is applied to only the upper catalyst layer of the membrane electrode assembly while the lower catalyst layer of the membrane electrode assembly is insulated, tensioners connected to the respective clampers to provide tensile force required to increase a distance between the clampers, and a measurer electrically connected to the upper catalyst layer of the membrane electrode assembly and serving to measure variation in electrical resistance at the upper catalyst layer of the membrane electrode assembly as the tensioners are operated.

Each of the clampers may include a clamper main body formed of an insulation material, the clamper main body having a seating recess formed to a prescribed depth in an upper surface thereof, and a specimen recess formed to a greater depth than the thickness of the seating recess in a middle region of the seating recess for seating of the membrane electrode assembly, a conductive cover formed of a conductive material, the conductive cover being seated in the seating recess of the clamper main body so as to be connected to the upper catalyst layer of the membrane electrode assembly, a bonding member formed of an insulation material, the bonding member being disposed between the specimen recess and the lower catalyst layer of the membrane electrode assembly, and a coupling member configured to couple the conductive cover to the clamper main body.

Each of the tensioners may include a rod fixed to a corresponding one of the clampers, and a cylinder body configured to operate the rod so as to increase the distance between the clampers.

The image capture unit may be an optical microscope.

In accordance with another aspect of the present invention, a method for predicting the extent of generation of micro-cracks in a membrane electrode assembly for a fuel cell, the membrane electrode assembly being formed with an upper catalytic layer and a lower catalytic layer on an upper surface and a lower surface of a polymer electrolyte membrane, including steps of: fabricating a specimen of the membrane electrode assembly, measuring variation in electrical resistance at a selected one of the upper catalyst layer and the lower catalyst layer of the fabricated specimen while tensioning the specimen, capturing, in real time, an image of micro-cracks generated in the catalyst layer, the variation in electrical resistance of which being measured, generating data pertaining to the size of micro-cracks based on variation in electrical resistance by detecting, in real time, the measured variation in electrical resistance corresponding to the captured image of micro-cracks, and interpreting the size of micro-cracks generated in the specimen based on the detected variation in electrical resistance, and predicting the extent of generation of micro-cracks in a new membrane electrode assembly by measuring variation in electrical resistance at a selected one of an upper catalyst layer and a lower catalyst layer of the new membrane electrode assembly while the membrane electrode assembly is tensioned, and comparing the measured variation in electrical resistance with the generated data.

The data pertaining to the size of micro-cracks based on the variation in electrical resistance may be generated by repeatedly implementing the fabricating, measuring, and capturing steps.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present invention may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Reference will now be made in detail to the preferred embodiments of the present invention, examples of which are illustrated in the accompanying drawings. Wherever possible, the same reference numbers will be used throughout the drawings to refer to the same or like parts.

Figure 1:
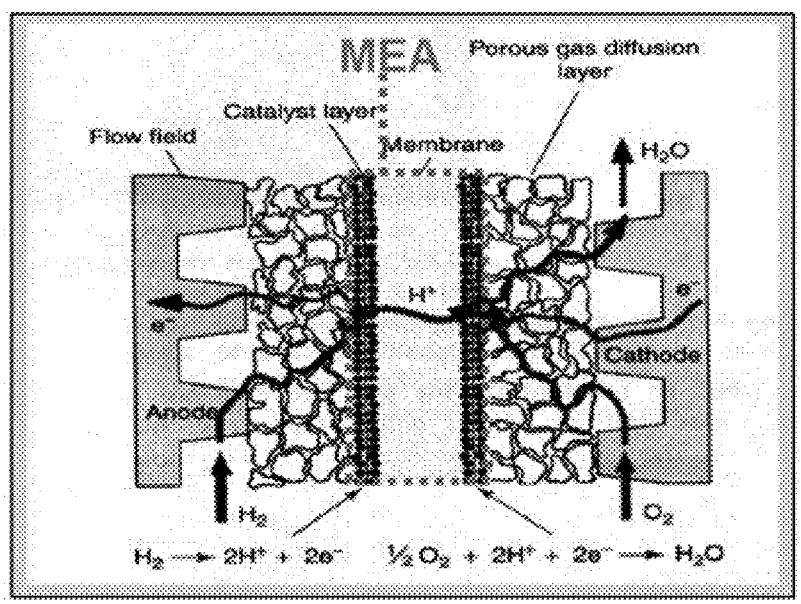
FIG. 1 (RELATED ART) is a view illustrating the basic configuration of a membrane electrode assembly for a fuel cell.
Figure 2:
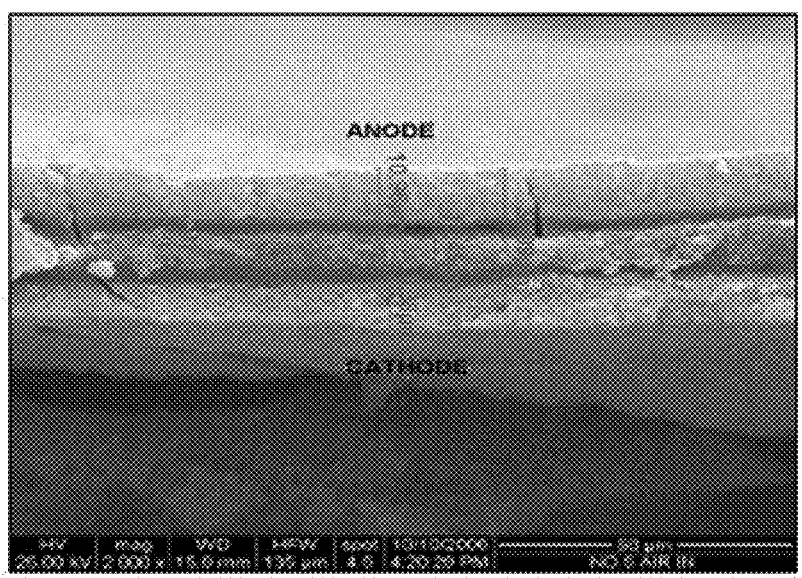
FIG. 2 (RELATED ART) is an SEM analytic image illustrating the configuration of the membrane electrode assembly for the fuel cell.
Figure 3:
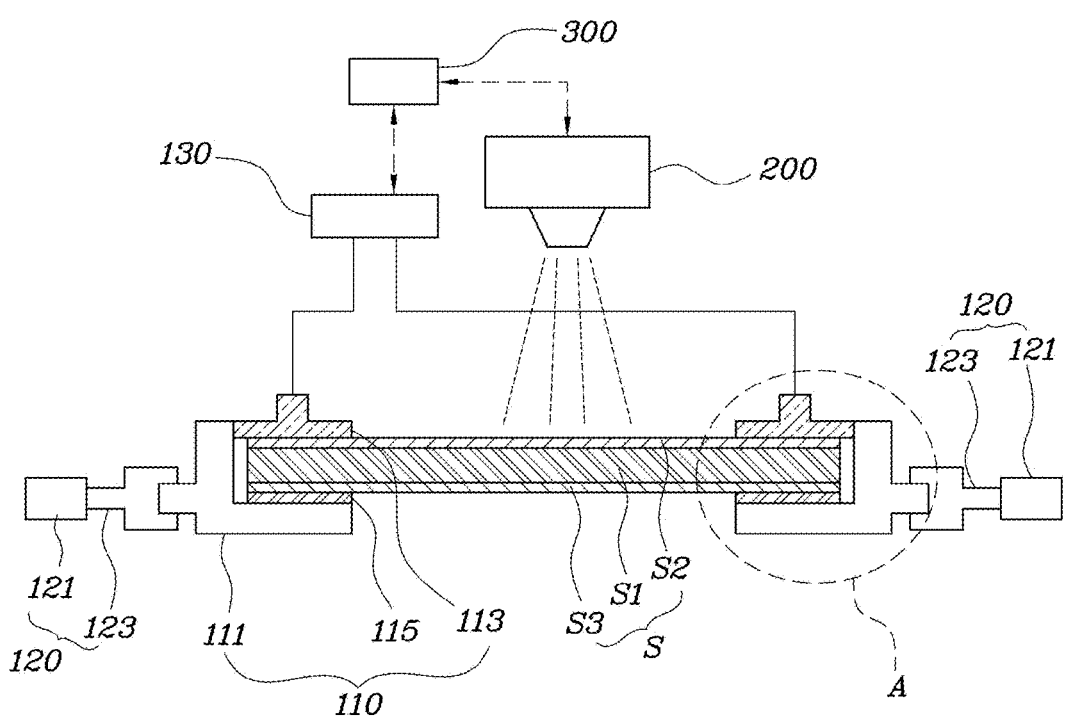
FIG. 3 is a view illustrating the configuration of the apparatus for measuring micro-cracks in a membrane electrode assembly according to an embodiment of the present invention.
Figure 4:
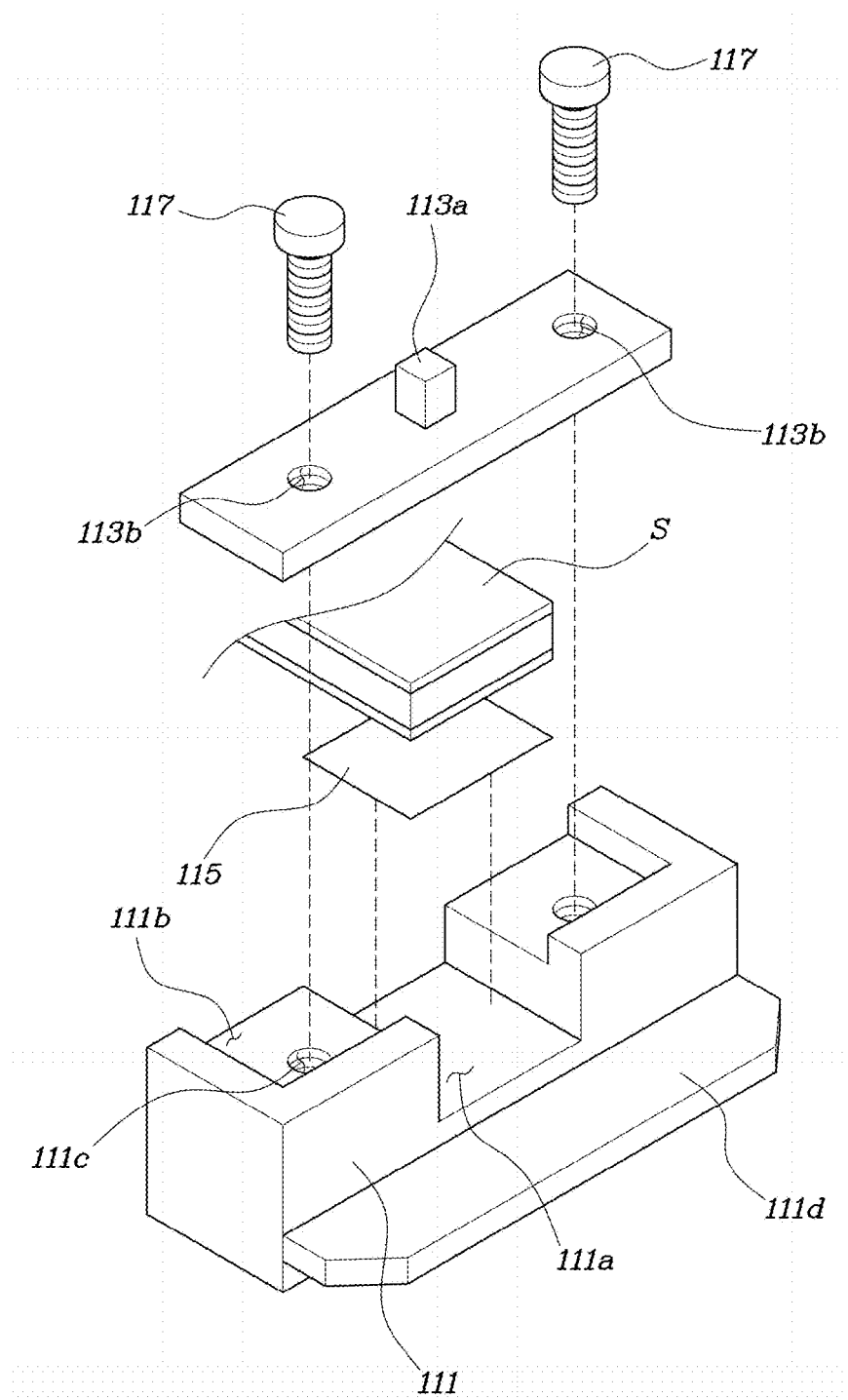
FIG. 4 is a perspective view illustrating a clamper of the apparatus for measuring micro-cracks in a membrane electrode assembly according to the embodiment of the present invention.

FIG. 3 is a view illustrating the configuration of the apparatus for measuring micro-cracks in a membrane electrode assembly according to an embodiment of the present invention, and FIG. 4 is a perspective view illustrating a clamper of the apparatus for measuring micro-cracks in a membrane electrode assembly according to the embodiment of the present invention.

First, in order to explain the present invention, the configuration of a membrane electrode assembly, which is an object to be measured, will be described in brief.

As exemplarily illustrated in FIG. 3, the membrane electrode assembly S is a constituent element that is applied to a stack of a fuel cell consisting of hundreds of unit cells. Each unit cell includes, for example, a Membrane Electrode Assembly (MEA), a Gas Diffusion Layer (GDL), and a separator, and functions to generate electricity.

Here, the membrane electrode assembly S includes a polymer electrolyte membrane S1 and catalyst layers S2 and S3 formed on both surfaces of the polymer electrolyte membrane S1.

In addition, the present invention has been proposed based on the fact that an increase in electrical resistance depends on an increase in the quantity (number) of micro-cracks generated in the catalyst layers S2 and S3. More specifically, increased electrical resistance signifies the generation of micro-cracks. In addition, as the strain rate (elongation) of the catalyst layers S2 and S3 increases, variation in electrical resistance also increases.

Meanwhile, as exemplarily illustrated in FIGS. 3 and 4, an apparatus for measuring micro-cracks in a membrane electrode assembly according to an embodiment of the present invention basically includes a resistance measurement unit 100, an image capture unit 200, and a controller 300.

The resistance measurement unit 100 is a unit that measures variation in the electrical resistance of the membrane electrode assembly S. The resistance measurement unit 100 serves to clamp the upper catalyst layer S2 and the lower catalyst layer S3 of the membrane electrode assembly S, and maintains the state in which power is applied to only one of the upper catalyst layer S2 and the lower catalyst layer S3 of the membrane electrode assembly S while the other layer remains insulated. For example, the resistance measurement unit 100 measures variation in the electrical resistance of the membrane electrode assembly S while tensioning both sides of the membrane electrode assembly S in the state in which power is applied to only the upper catalyst layer S2 of the membrane electrode assembly S and the lower catalyst layer S3 of the membrane electrode assembly S is insulated.

The resistance measurement unit 100 includes a pair of clampers 110 to clamp both sides of the membrane electrode assembly S, tensioners 120 connected to the respective clampers 110 so as to provide tensile force, which is required to increase the distance between the clampers 110, and a measurer 130 to measure variation in electrical resistance at the upper catalyst layer S2 of the membrane electrode assembly S.

The clampers 110 serve to clamp both sides of the membrane electrode assembly S in the state in which power is applied to only the upper catalyst layer S2 of the membrane electrode assembly S while the lower catalyst layer S3 of the membrane electrode assembly S is insulated.

Each of the clampers 110 includes a clamper main body 111, a conductive cover 113, a bonding member 115, and coupling members 117.

The clamper main body 111 serves to clamp and insulate the membrane electrode assembly S. The clamper main body 111 is formed of an insulation material and has a seating recess 111b formed to a prescribed depth in the upper surface thereof. At this time, the depth of the seating recess 111b may correspond to the thickness of the conductive cover 113.

In addition, a specimen recess 111a is formed in the middle region of the seating recess 111b. The specimen recess 111a is deeper than the seating recess 111b so as to seat the membrane electrode assembly S. At this time, the depth of the seating recess 111b may correspond to the thickness of the membrane electrode assembly S such that the conductive cover 113 is electrically connected to the upper catalyst layer S2 of the membrane electrode assembly S.

In addition, a pair of coupling recesses 111c for fixing of the conductive cover 113 is formed in both edge regions of the seating recess 111b.

In addition, a clamper haft 111d protrudes from the rear end of the clamper main body 111 for easy connection with the tensioner 120.

The conductive cover 113 serves to apply pressure to the upper catalyst layer S2 of the membrane electrode assembly S so as to electrically connect and clamp the membrane electrode assembly S to the clamper main body 111. As such, the conductive cover 113 may be configured in the form of a plate using a conductive material, and may have a shape corresponding to the shape of the seating recess 111b.

The conductive cover 113 is formed, in both edge regions thereof, with coupling holes 113b, which communicate with the coupling recesses 111c formed in the clamper main body 111.

In addition, the conductive cover 113 may be formed at the upper surface thereof with a protrusion 113a. The protrusion 113a protrudes upward to facilitate easy connection with the measurer 130, which will be described below.

The bonding member 115 serves to bond the membrane electrode assembly S to the specimen recess 111a of the clamper main body 111. The bonding member 115 is disposed between the specimen recess 111a of the clamper main body 111 and the lower catalyst layer S3 of the membrane electrode assembly S. At this time, the bonding member 115 may have an insulation property. A double-sided tape may be used as the bonding member 115, so as to allow the membrane electrode assembly S to be detachably attached to the upper surface of the specimen recess 111a.

The coupling members 117 serve to fix the conductive cover 113 to the seating recess 111b of the clamper main body 111. The coupling members 117 may be bolts fastened through the coupling recesses 111c in the clamper main body 111 and the coupling holes 113b of the conductive cover 113. In the case where bolts are used as the coupling members 117, the coupling recesses 111c and the coupling holes 113b require screw threads formed in the inner circumferential surfaces thereof.

The tensioners 120 are connected to the respective clamps 110, and serve to provide tensile force required to increase the distance between the clampers 110. The tensioners 120 may be selected from among various types of tensioning devices. For example, in the present embodiment, each of the tensioners 120 may include a rod 123 fixed to a corresponding one of the clampers 110, and a cylinder body 121 configured to operate the rod 123 so as to increase the distance between the clampers 110. At this time, the cylinder body 121 may be hydraulically or pneumatically operated in order to precisely control the operation of the rod 123.

The measurer 130 is electrically connected to the upper catalyst layer S2 of the membrane electrode assembly S, and serves to measure variation in electrical resistance at the upper catalyst layer S2 of the membrane electrode assembly S as the tensioners 120 are operated. The measurer 130 may be selected from among various means that are capable of measuring variation in electrical resistance.

Meanwhile, in the present embodiment, the image capture unit 200 is provided to directly capture, in real time, the extent of generation of micro-cracks, corresponding to variation in electrical resistance, attributable to the generation of micro-cracks in the membrane electrode assembly S.

The image capture unit 200 is disposed directly above the membrane electrode assembly S, which is tensioned in the resistance measurement unit 100, and serves to capture an image of micro-cracks generated in the upper catalyst layer S2 of the membrane electrode assembly S. To this end, the image capture unit 200 may use an optical microscope that is capable of measuring micro-cracks.

Meanwhile, the controller 300 is a unit that detects, in real time, variation in electrical resistance, measured by the resistance measurement unit 100, corresponding to the image of micro-cracks captured by the image capture unit 200, and interprets the size of micro-cracks generated in the membrane electrode assembly S based on the detected variation in electrical resistance.

Next, the state of use of the apparatus for measuring micro-cracks in the membrane electrode assembly according to the embodiment of the present invention having the above-described configuration will be described.

First, to measure micro-cracks in the membrane electrode assembly S, the membrane electrode assembly S is fabricated into a specimen S in the form of a bar.

Subsequently, the specimen S is seated in the specimen recesses 111a of the clamper main bodies 111 connected to the tensioners (e.g., a Delaminator Adhesion Test System from DTS Co., USA) 120 such that the surface S, which is an electrical resistance variation measurement target surface, faces upward. At this time, for stronger fixing, the bonding member 115 is interposed between the specimen S and the clamper main body 111.

Subsequently, the conductive cover 113 is seated in the seating recess 111b and then fixed to the seating recess 111b using the coupling members 117. At this time, the lower surface of the conductive cover 113 comes into contact with the upper surface of the specimen S to achieve electrical connection therebetween.

After the specimen S is completely fixed, the image capture unit (e.g., a VHX-1000 digital microscope from KEYENCE Co., USA) 200 is disposed directly above the specimen S, and the measurer (e.g., a Model 2000 digital multi-meter from KEITHLEY Instruments Inc., USA) 130 is connected to the conductive cover 113.

When the measurement of variation in the electrical resistance of the specimen S is completely prepared, the variation in electrical resistance is measured by using the measurer 130 while the specimen S is tensioned using the tensioners 120, and the image capture unit 200 captures, in real time, an image of micro-cracks generated, by tensioning, in the specimen S. The measured variation in electrical resistance and the image of micro-cracks are transmitted to the controller 300 so as to be analyzed and stored in the controller 300.

Here, variation in electrical resistance is calculated using the following Equation 1.

$$\text{Variation in Electrical Resistance}[\%] = \frac{R - R_0}{R_0} \times 100 \quad \text{Equation 1}$$

Here, $R_0$ refers to the initially measured electrical resistance value, and R refers to a resultant electrical resistance value measured every second.

Meanwhile, a method for predicting the generation of micro-cracks in the membrane electrode assembly using the apparatus for measuring micro-cracks in the membrane electrode assembly according to the embodiment of the present invention having the above-described configuration will be described below.

First, a process of generating data pertaining to the size of micro-cracks based on variation in electrical resistance is repeatedly implemented.

More specifically, the specimen S of the membrane electrode assembly is fabricated (First Step).

Subsequently, variation in electrical resistance at any one catalyst layer (e.g., the upper catalyst layer S2) selected from among the upper catalyst layer S2 and the lower catalyst layer S3 of the specimen S is measured while the fabricated specimen S is tensioned (Second Step).

Subsequently, an image of micro-cracks generated in the upper catalyst layer S2, the variation in electrical resistance of which has been measured in the second step, is captured (Third Step).

Data pertaining to the size of micro-cracks based on the variation in electrical resistance is generated by detecting, in real time, the variation in electrical resistance, measured in the second step, which corresponds to the image of micro-cracks captured in the third step, and interpreting the size of micro-cracks generated in the specimen S based on the detected variation in electrical resistance (Fourth Step).

As described above, in the fourth step, the first step to the third step may be repeatedly implemented to generate data pertaining to the size of micro-cracks based on the variation in electrical resistance.

When the data pertaining to the size of micro-cracks based on the variation in electrical resistance has been completely generated, in order to predict the extent of generation of micro-cracks in the membrane electrode assembly, variation in the electrical resistance of a selected one of an upper catalyst layer and a lower catalyst layer of a new membrane electrode assembly is measured while the membrane electrode assembly is tensioned, and the measured variation in electrical resistance is compared with the data generated in the fourth step in order to predict the extent of generation of micro-cracks in the membrane electrode assembly, the variation in electrical resistance of which has been measured, (Fifth Step).

As is apparent from the above description, according to the embodiment of the present invention, in a membrane electrode assembly for a fuel cell, which consists of a polymer electrolyte membrane and catalyst layers, it is possible to quantitatively measure the generation of micro-cracks and the extent of growth of micro-cracks, which have a great effect on the durability of a stack, in the catalyst layers.

In addition, it is possible to accurately predict the generation of micro-cracks and the extent of growth of micro-cracks in the catalyst layer in a non-destructive and quantitative manner using measured data.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for measuring micro-cracks in a membrane electrode assembly for a fuel cell, the membrane electrode assembly being formed with an upper catalytic layer and a lower catalytic layer on an upper surface and a lower surface of a polymer electrolyte membrane, respectively, the apparatus comprising:
a resistance measurement unit configured to clamp the upper catalyst layer and the lower catalyst layer of the membrane electrode assembly, the resistance measurement unit serving to measure variation in electrical resistance of the membrane electrode assembly while tensioning both sides of the membrane electrode assembly in a state in which power is applied to both end parts of only the upper catalyst layer of the membrane electrode assembly while the lower catalyst layer of the membrane electrode assembly is insulated;
an image capture unit disposed directly above the membrane electrode assembly and serving to capture an image of micro-cracks generated in the upper catalyst layer of the membrane electrode assembly while the membrane electrode assembly is being tensioned by the resistance measurement unit; and
a controller configured to detect, in real time, the variation in electrical resistance, measured by the resistance measurement unit, corresponding to the image of micro-cracks captured by the image capture unit, and to interpret the size of the micro-cracks generated in the membrane electrode assembly based on the detected variation in electrical resistance.

2. The apparatus according to claim 1, wherein the resistance measurement unit includes:
a pair of dampers configured to clamp both sides of the membrane electrode assembly in the state in which power is applied to only the upper catalyst layer of the membrane electrode assembly while the lower catalyst layer of the membrane electrode assembly is insulated;
tensioners connected to the respective dampers to provide tensile force required to increase a distance between the dampers; and
a measurer electrically connected to the upper catalyst layer of the membrane electrode assembly and serving to measure variation in electrical resistance at the upper catalyst layer of the membrane electrode assembly as the tensioners are operated.

3. The apparatus according to claim 2, wherein each of the dampers includes:
a damper main body formed of an insulation material, the damper main body having a seating recess formed to a prescribed depth in an upper surface thereof, and a specimen recess formed to a greater depth than the thickness of the seating recess in a middle region of the seating recess for seating of the membrane electrode assembly;
a conductive cover formed of a conductive material, the conductive cover being seated in the seating recess of the damper main body so as to be connected to the upper catalyst layer of the membrane electrode assembly;
a bonding member formed of an insulation material, the bonding member being disposed between the specimen recess and the lower catalyst layer of the membrane electrode assembly; and
a coupling member configured to couple the conductive cover to the damper main body.

4. The apparatus according to claim 2, wherein each of the tensioners includes:
a rod fixed to a corresponding one of the dampers; and
a cylinder body configured to operate the rod so as to increase the distance between the dampers.

5. The apparatus according to claim 1, wherein the image capture unit is an optical microscope.

6. A method for predicting the extent of generation of micro-cracks in a membrane electrode assembly for a fuel cell, the membrane electrode assembly being formed with an upper catalytic layer and a lower catalytic layer on an upper surface and a lower surface of a polymer electrolyte membrane, respectively, the method comprising the steps of:
fabricating a specimen of the membrane electrode assembly;
measuring variation in electrical resistance at both end parts of only a selected one of the upper catalyst layer and the lower catalyst layer of the fabricated specimen while tensioning the specimen, while an unselected one of the upper catalyst layer and the lower catalyst layer is insulated;
capturing, in real time, an image of micro-cracks generated in the catalyst layer, the variation in electrical resistance of which being measured;
generating data pertaining to the size of micro-cracks based on variation in electrical resistance by detecting, in real time, the measured variation in electrical resistance corresponding to the captured image of micro-cracks, and interpreting the size of micro-cracks generated in the specimen based on the detected variation in electrical resistance; and
predicting the extent of generation of micro-cracks in a new membrane electrode assembly by measuring variation in electrical resistance at a selected one of an upper catalyst layer and a lower catalyst layer of the new membrane electrode assembly while the membrane electrode assembly is tensioned, and comparing the measured variation in electrical resistance with the generated data.

7. The method according to claim 6, wherein the data pertaining to the size of micro-cracks based on the variation in electrical resistance is generated by repeatedly implementing the steps of fabricating, measuring, and capturing.

* * * * *